US009579231B2

(12) United States Patent
Galvin

(10) Patent No.: US 9,579,231 B2
(45) Date of Patent: Feb. 28, 2017

(54) ORTHOPEDIC TOE GUARD

(71) Applicant: Scott Thomas Galvin, Manzanita, OR (US)

(72) Inventor: Scott Thomas Galvin, Manzanita, OR (US)

(73) Assignee: Scott Thomas Galvin, Manzanita, OR (US)

( * ) Notice: Subject to any disclaimer, the term of this patent is extended or adjusted under 35 U.S.C. 154(b) by 143 days.

(21) Appl. No.: 14/695,524

(22) Filed: Apr. 24, 2015

(65) Prior Publication Data
US 2016/0310312 A1    Oct. 27, 2016

(51) Int. Cl.
A61F 5/00      (2006.01)
A61F 5/37      (2006.01)

(52) U.S. Cl.
CPC ..................... A61F 5/37 (2013.01)

(58) Field of Classification Search
CPC ........ A61F 5/37; A61F 13/041; A61F 5/0195; A43B 3/0052; A43B 23/081; A43B 23/087; A45D 29/22; A45D 2029/008
USPC .......................................................... 602/30
See application file for complete search history.

(56) References Cited

U.S. PATENT DOCUMENTS

| 3,263,679 | A |   | 8/1966  | Haas |
|-----------|---|---|---------|------|
| 3,583,397 | A | * | 6/1971  | Baddour ................. A61F 5/04 24/710.8 |
| 3,643,659 | A | * | 2/1972  | Storer .................. A61F 5/0195 128/882 |
| 3,773,041 | A | * | 11/1973 | Bogar, Jr. ............ A61F 13/041 602/10 |
| 3,832,997 | A | * | 9/1974  | Cappelletti ........... A61F 13/041 602/11 |
| 4,177,583 | A |   | 12/1979 | Chapman |
| 4,271,605 | A |   | 6/1981  | Raczka |
| 4,409,970 | A | * | 10/1983 | Carrel .................. A61F 13/041 602/40 |
| 4,454,872 | A |   | 6/1984  | Brouhard |
| 4,566,208 | A |   | 1/1986  | Shaffner |
| 4,940,046 | A |   | 7/1990  | Jacoby |
| 5,031,608 | A |   | 7/1991  | Weinstein |
| 5,095,897 | A |   | 3/1992  | Clark |
| 5,300,075 | A |   | 4/1994  | Gordon |
| 5,462,069 | A |   | 10/1995 | Cohen |
| 5,752,952 | A |   | 5/1998  | Adamson |
| 5,980,475 | A |   | 11/1999 | Gibbons |
| 6,514,222 | B2 | * | 2/2003 | Cook .................. A61F 5/05866 602/20 |
| 6,802,318 | B1 |   | 10/2004 | Parker |
| 6,836,980 | B2 |   | 1/2005  | Woods |
| 2015/0342773 | A1 | * | 12/2015 | Wargula ................ A61F 5/01 602/5 |

* cited by examiner

Primary Examiner — Kristen Matter

(57) ABSTRACT

An Orthopedic Toe Guard is a single piece of Stainless Steel Tube, bent to protrude forward of the toes when mounted to the sides of the cast.

2 Claims, 2 Drawing Sheets

ORTHOPEDIC TOE GUARD

TECHNICAL FIELD

The Orthopedic Toe Guard relates to toe protection of the types adapted to be mounted to hard and soft casts.

BACKGROUND

Prior Art

Toe Protectors have been devised to provide foot protection for the human foot. Examples of toe protective devices are illustrated in U.S. Pat. Nos. 68,366,980, 6,802,318, 5,980,475, 5,420,69, 4,177,583, 3,263,679. These examples generally are cup shaped fixtures that are added to a boot and provide very little air movement around the toes and do not allow for inspection of the injured toes. The advantage of the Orthopedic Toe Guard is that it is designed for a foot cast and it provides very good air movement around the toes.

Other foot protective devices have been devised with the use of rails embedded in orthopedic casting as illustrated in U.S. Pat. Nos. 5,095,897, 5,031,608, 4,940,046. These examples although they provided very good air movement they are not designed for use of metal that can be autoclaved and appear they would be very expensive to build.

Toe splints have been devised as illustrated in U.S. Pat. Nos. 5,095,897, 5,031,608, 4,940,046. The disadvantage of the toe splint is they provide poor air movement around the injured toe and they are expensive to fabricate.

Surgical Pin devices have been devised as illustrated in U.S. Pat. Nos. 5,729,52, 5,300,075. These devices do not provide good air movement around the injured toe and do not address the issue of a sterile environment of post-surgery.

In general, toe protectors have been rather bulky and costly to manufacture. It would be distinct advances in the art were a toe guard to be devised that could be mounted to a hard or soft cast while possessing the attributes of simplicity and economy. It is the advantage of the Orthopedic Toe Guard to provide simplicity with durability and provide a product that can address the sterile environment of post-surgical procedures.

SUMMARY OF THE INVENTION

Briefly described, the present art comprises a toe protector manufactured to provide protection of toes of a human foot. The object of this art is to provide protection for the toes of a human foot that is inexpensive to construct and easy to mount to a hard and soft cast. The material was selected so the art can be autoclaved to guarantee a sterile product should it need to enter a surgical operating room. The material and the configuration also provide superior strength to protect the toes from any forward impact.

DRAWINGS

References Numbers

1 Seal Welded
2 Stainless Steel Tube
3 Mechanically Bent
4 Orthopedic Toe Guard
5 Surgical pin
6 Fiberglass Casting Material or Medical Tape
7 Orthopedic Toe Guard embedded in hard or soft cast
8 Cast Padding

DETAILED DESCRIPTION

Figure 1:
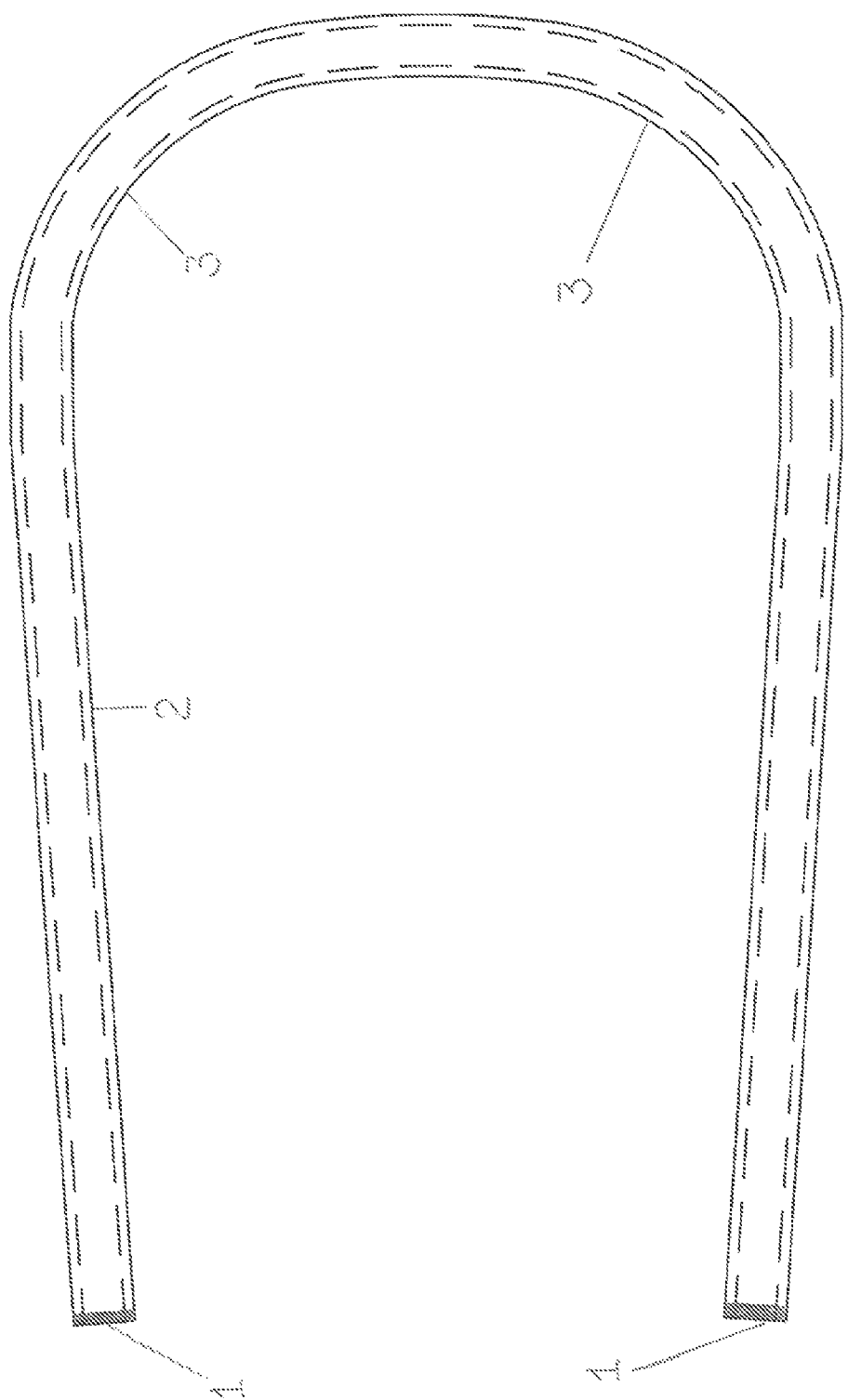
FIG. 1 shows a top view of the bent stainless steel tube.

Referring now in more detail to the drawings, in which like numbers indicate like parts throughout several views. FIG. 1 illustrates the Orthopedic Toe Guard. FIG. 1, 2 illustrates Stainless Steel tube. FIG. 1, 1 illustrates seal welded end cap. The seal welding of the ends 1 will ensure that the Orthopedic Toe Guard can be autoclaved. To achieve the shape to conform around the cast the stainless steel tube will be mechanically bent 3.

Figure 2:
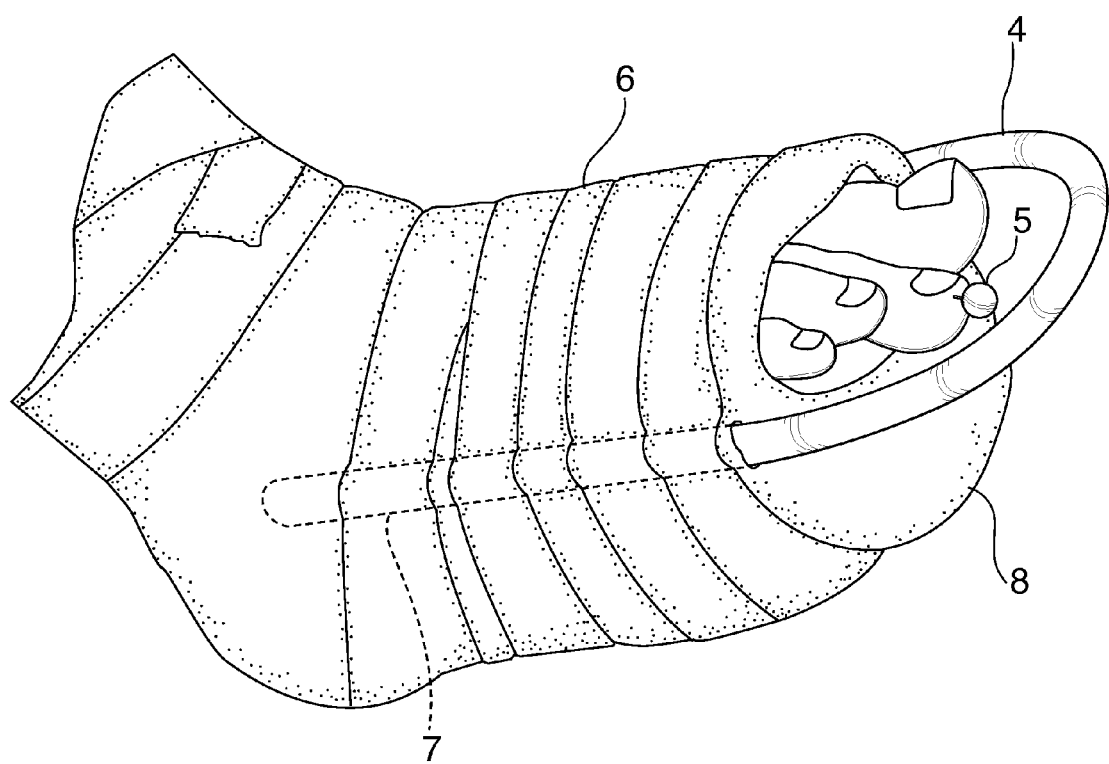
FIG. 2 shows an isometric view of the Orthopedic Toe Guard mounted to a hard or soft cast.

FIG. 2 illustrates the Orthopedic Toe Guard 4 as it is mounted to either a hard or soft cast 6. The Orthopedic Toe guard is embedded 7 in the casting material 6 to provide protection of the surgical pin 5. For purpose of illustration cast padding 8 is shown.

The invention claimed is:

1. A wrap around toe protector consisting of: an orthopedic cast configured for use on a human foot and a single piece of stainless steel tube with an end cap on each end of the tube, the tube bent to form a generally U shape, each said end of the tube attached to the cast, the tube configured to extend in a horizontal plane from an ankle area on the foot and forward of the toe being protected in order to protect the toes from forward impact.

2. The wrap around toe protector of claim 1 wherein said toe protector is capable of being sterilized by autoclave methods.

* * * * *